United States Patent
Jensen et al.

(10) Patent No.: US 10,034,760 B2
(45) Date of Patent: Jul. 31, 2018

(54) REINFORCEMENT IMPLANT FOR LAMINA WITH A CANTILEVER BRIDGE PART

(71) Applicant: FACET-LINK INC., Rockaway, NJ (US)

(72) Inventors: Harm-Iven Jensen, Noer (DE); Helmut D. Link, Hamburg (DE)

(73) Assignee: FACET-LINK INC., Rockaway, NJ (US)

( * ) Notice: Subject to any disclaimer, the term of this patent is extended or adjusted under 35 U.S.C. 154(b) by 466 days.

(21) Appl. No.: 13/852,597

(22) Filed: Mar. 28, 2013

(65) Prior Publication Data

US 2014/0188223 A1 Jul. 3, 2014

Related U.S. Application Data

(60) Provisional application No. 61/616,650, filed on Mar. 28, 2012.

(51) Int. Cl.
| | |
|---|---|
| *A61F 2/44* | (2006.01) |
| *A61B 17/70* | (2006.01) |
| *A61B 17/80* | (2006.01) |
| *A61B 17/86* | (2006.01) |

(52) U.S. Cl.
CPC .......... *A61F 2/44* (2013.01); *A61B 17/7064* (2013.01); *A61B 17/7071* (2013.01); *A61B 17/8047* (2013.01); *A61F 2/4405* (2013.01); *A61B 17/7067* (2013.01); *A61B 17/863* (2013.01)

(58) Field of Classification Search
CPC ............ A61B 17/7064; A61B 17/7067; A61B 17/7071; A61F 2/4405
USPC ................................................. 606/247–249
See application file for complete search history.

(56) References Cited

U.S. PATENT DOCUMENTS

| | | | |
|---|---|---|---|
| 2005/0251138 A1* | 11/2005 | Boris | A61B 17/808 623/17.11 |
| 2007/0185489 A1 | 8/2007 | Abdou | |
| 2008/0215096 A1* | 9/2008 | Nash | A61B 17/8042 606/249 |
| 2008/0255619 A1* | 10/2008 | Schneiderman | A61B 17/7007 606/276 |

(Continued)

FOREIGN PATENT DOCUMENTS

| | | |
|---|---|---|
| WO | WO-2005/096969 | 10/2005 |
| WO | WO-2011/040983 | 4/2011 |
| WO | WO-2012/041914 | 4/2012 |

*Primary Examiner* — Nicholas Plionis
(74) *Attorney, Agent, or Firm* — Morrison & Foerster LLP

(57) ABSTRACT

A reinforcement implant comprises a cantilever part for spanning a resected area of a lamina and an anchoring part at opposite ends of the cantilever part. The first anchoring part has a pressure surface for bearing on the spinous process of the vertebra, and the second anchoring part has a transverse thrust surface for bearing on an outer face of the lamina. The pressure surface and the transverse thrust surface enclose an obtuse angle. An anti-shear device (e.g., a facet screw) is arranged on the transverse thrust surface, and one edge of the transverse thrust surface is adjoined by a load-bearing area of the cantilever part. The implant can thus be mounted in place from outside without needing to be pushed with a load-bearing action into the resected area. The resection surfaces on the lamina are free of loads, such that unevenness does not cause problems.

15 Claims, 4 Drawing Sheets

(56) References Cited

U.S. PATENT DOCUMENTS

| | | | |
|---|---|---|---|
| 2008/0294260 A1* | 11/2008 | Gray | A61F 2/4455 623/17.16 |
| 2009/0138053 A1* | 5/2009 | Assell | A61F 2/4405 606/301 |
| 2010/0069960 A1* | 3/2010 | Chaput | A61B 17/7071 606/249 |
| 2011/0106083 A1 | 5/2011 | Voellmicke et al. | |
| 2011/0172666 A1 | 7/2011 | Heilman | |
| 2011/0184470 A1* | 7/2011 | Gorek | A61B 17/7011 606/279 |
| 2012/0022603 A1 | 1/2012 | Kirschman | |
| 2012/0071923 A1 | 3/2012 | Perez-Cruet et al. | |
| 2012/0071931 A1* | 3/2012 | Perez-Cruet | A61B 17/7071 606/279 |

* cited by examiner

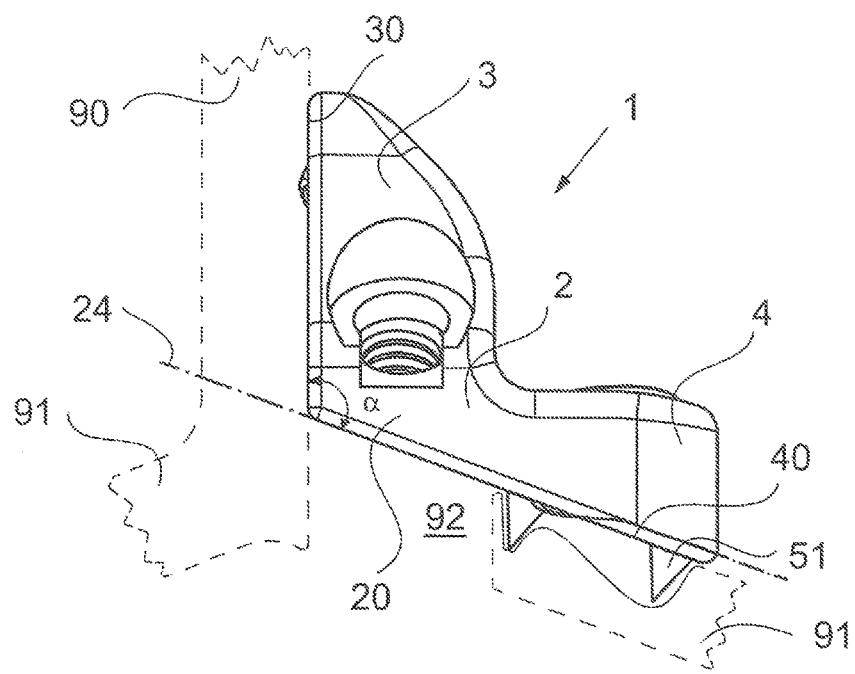
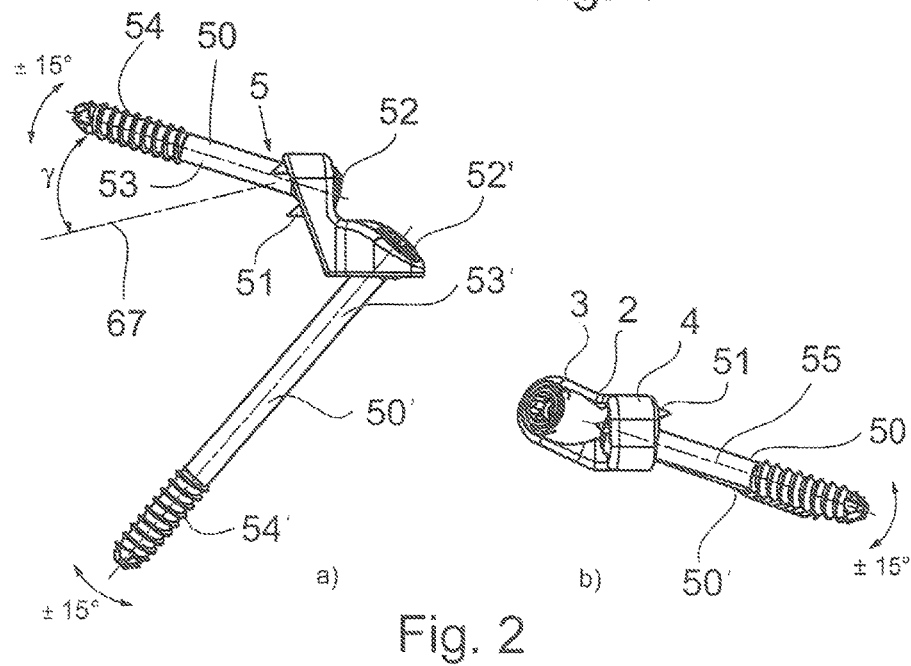
Fig. 1
Fig. 2

REINFORCEMENT IMPLANT FOR LAMINA WITH A CANTILEVER BRIDGE PART

REFERENCE TO RELATED APPLICATIONS

This application claims the benefit of U.S. Provisional Patent Application No. 61/616,650, filed on Mar. 28, 2012, the contents of which are incorporated herein by reference.

FIELD OF THE INVENTION

The invention relates to a reinforcement implant for lamina with a cantilever bridge part.

BACKGROUND OF THE INVENTION

The spinal columns of humans or animals are constructed from a plurality of vertebrae arranged one above another. They are interconnected both in a load-bearing manner and also in an articulated manner. For this purpose, the vertebrae have a structure with a solid vertebral body with two osseous projections (pedicles) which protrude laterally and to the rear and which, in their rear region, are connected by an osseous arch. In the connection area, the osseous arch is broadened (lamina) and has, at its center, a rearwardly protruding spinous process. The spinous process and two further transverse processes on the side surfaces of the pedicles form articulation points for muscles and ligaments. In the area where the pedicles merge into the lamina, an upper and a lower articulating process are arranged on each side. These each form part of a facet joint with an adjacent upper or lower vertebra. For load-bearing connection to the adjacent upper and lower vertebra, intervertebral disks are in each case provided which are arranged at the bottom and/or top on relatively flat cover surfaces of the vertebral body. The space bounded by the rear side of the vertebral body and by the vertebral arch forms a hollow space (spinal canal) in which nerve fibers running parallel to the spinal column are accommodated. It has been found that pressure is exerted on the nerve fibers when they become pinched or trapped, particularly on account of osseous growth in the area of the spinal canal or on account of protrusions of the intervertebral disk (so-called herniated disk), and that this may cause severe back pain.

For therapy, it is known to at least partially open the vertebral arch in order to create an access route to the spinal canal. There, the growths causing the problems are removed by means of instruments known per se, and the pressure is thus removed from the nerve fibers. The pain induced by the pressure is in this way correspondingly reduced. In this method, also known as laminectomy or decompression, the access created in the lamina, that is to say the opening present therein, is in most cases not closed after the operation. It has been shown that this weakens the mechanical stability of the vertebra.

It has been proposed by the applicant, in an earlier patent application, to make available an implant set comprising reinforcement implants in various sizes. They have a rhombus-shaped filler body which is inserted into and fills the opening created by the laminectomy. The rhombus-shaped filler body bears with its two opposite side surfaces on the resection surfaces of the lamina. In this way, the laminar arch is again made complete by the insertion of the filler body, such that it can again bear loads and, in particular, does not collapse under compressive loads. To be able to fill the resected area as completely as possible and without expanding it, the reinforcement implant has to be provided in a considerable number of different sizes (at least seven) per side (left or right). This means considerable complexity of the implant set. Moreover, for the desired function of transfer of pressure, it is important that the lateral faces of the filler body lie as flat as possible on the resection surfaces of the lamina. Since the resection surfaces are often not quite plane in practice, the transfer of pressure is impaired. Another consideration is that the insertion of the filler body is made difficult when the resection surfaces are not plane, and this causes additional complications.

SUMMARY OF THE INVENTION

An object of the invention is to make available an improved reinforcement implant that avoids these disadvantages.

A solution according to the invention lies in the characteristics as broadly described herein. Advantageous improvements are the subject matter of the detailed embodiments described below.

A reinforcement implant for insertion into the lamina of a vertebra, comprising a main body with bearing surfaces on the vertebra and a fastening device, is provided, according to the invention, with a cantilever part for spanning a resected part, and also, at opposite ends of the cantilever part, in each case with an anchoring part, wherein a first anchoring part is designed with a pressure surface for bearing on the spinous process of the vertebra, and a second anchoring part is designed with a transverse thrust surface for bearing on an outer face of the lamina, and the pressure surface and the transverse thrust surface enclose an obtuse angle, wherein an anti-shear device, in particular a facet screw, is arranged on the transverse thrust surface, and one edge of the transverse thrust surface is adjoined by a load-bearing area of the cantilever part for spanning the resected part of the lamina.

The invention is based on the concept of using the special anchoring parts to span the resected lamina segment with a durable bridge that is robust in practice and is also easy to implant. With the two bearing surfaces oriented at an obtuse angle to each other, namely the pressure surface on the one hand and the transverse thrust surface on the other hand, a holding arrangement is created that is secure in all spatial dimensions and is free of constraint. This design avoids static overdetermination, as is typical of implants (especially designed as filler bodies) with two mutually opposite pressure surfaces that lie substantially parallel to each other. The natural elasticity in the bone is taken up in this way and is thus preserved, instead of being limited by constraint. The implant thus behaves in a way that is more physiological. This is not only favorable in terms of behavior, but also means an increased useful life of the implant by avoiding degeneration. It has indeed been found that very stiff implants, which is what constraining implants are, easily lead to degeneration of the now unstressed bone.

Moreover, the implant according to the invention is easier to handle during the implantation itself. It does not need to be inserted into the free space created by the resection on the lamina, but is instead as it were mounted in place from the outside in order thereby to bridge the free space. For this purpose, the implant has, on one side, a pressure surface that is placed against a side face of the spinous process on the vertebra, and the implant has, on its other side, a transverse thrust surface that is placed on the outer face of the lamina and is fixed there with an anti-shear device. The implant does not therefore have to be pushed at all into the free space. It has no load-bearing contact even with the actual resection surfaces that were created by the resection in the lamina. Unevenness in the resection surface, which is in practice often unavoidable in surgery, therefore has no influence on the position and fastening of the implant.

The cantilever part of the reinforcement implant is preferably designed such that its area that transfers loading forces from the transverse thrust surface to the pressure surface does not intersect a plane defined by the transverse thrust surface. This means that the load-bearing area of the cantilever part does not protrude into the free space created by the resection on the lamina; the bridge part is thus located completely outside. It is thus possible to very largely avoid irritations that are caused by transfer of force from the transverse thrust surface to the pressure surface and affect the particularly sensitive resected area of the lamina.

The reinforcement implant is expediently designed such that the anchoring parts are in the form of a first limb and a second limb, which are connected via the cantilever part. This limb structure makes it possible to reduce the amount of material used and the space taken up by the implant. The space-saving design minimizes the effect on surrounding tissue and therefore the danger of irritations caused by the implant. A pivot joint for a fastening pin is preferably arranged on at least one of the limbs. A fastening pin is understood in particular as a screw or a bone nail. By means of this pivot joint, the axis of the fastening pin can be freely adjusted within certain limits. An adjustability through 15° in each direction with respect to a center position ("normal position") has proven suitable.

The pivot joint preferably has a cup-shaped receiving seat and, mounted in the latter, a ring through which the fastening pin is guided. The cup-shaped design provides a stepless pivotability, which has low friction in the relaxed state of the fastening pin and is self-locking in the tensioned state of the fastening pin.

It is particularly preferable if the ring has a rotation barrier, which holds it secure against rotation with respect to the receiving seat of the pivot joint. Undesired turning of the ring in the pivot joint is prevented with a rotation barrier of this kind. Undesired turning can customarily occur if the fastening pin is a screw and the screw is to be tightened. In doing so, it is unsuitable for the ring to turn too. With the rotation barrier, the ring is prevented from turning about the axis of the fastening pin, although the pivotability of the ring is not restricted.

The pivot joints are expediently designed such that the fastening pins are movable through at least 10° and at most 20° in each direction about the normal position. It has been found that a greater angle in the range of adjustment can weaken the reliability of the fastening and the accuracy of the positioning. By contrast, a smaller range of adjustment often fails to satisfy the requirements in respect of sufficient universality of the reinforcement implant according to the invention.

The pivot joints in the two limbs are preferably designed such that the fastening pins of the two limbs lie in one plane in the normal position. In this way, a fastening plane is covered that applies identically for both limbs. By contrast, static overdetermination, as would be present in a skewed arrangement of the fastening pins outside a common plane, could lead to constraints. This is effectively prevented by the arrangement in a common plane.

The anti-shear device is preferably in the form of a screw which is oriented such that, in its normal position, it deviates from a perpendicular of the transverse thrust surface by at most 30°, but preferably by at least 10°. It has been found that, with such an arrangement, two objectives can be combined with each other. One objective is to sufficiently secure the reinforcement implant according to the invention against undesired displacement relative to the lamina. The other objective is to orient the screw in such a way that it provides fastening in a mechanically robust part of the bone, in the continuation of which part lies the facet joint to the adjacent vertebra in the caudal direction (i.e. toward the base of the spinal column). By using a long screw, a so-called facet screw, which reaches into the adjacent lower vertebra, it is thus possible not only to achieve a fastening but at the same time also to fuse the facet joint. The facet joint is thereby immobilized on this side. If immobilization is not intended, a short screw suffices that does not reach into the adjacent lower vertebra.

On the cantilever part of the reinforcement implant, a wing extension can be provided which protrudes from an edge of the transverse thrust surface. The wing extension is preferably oriented parallel to the pressure surface. The wing extension is not itself load-bearing, and it protrudes into the free space that has been created in the lamina by the resection. It facilitates insertion of the implant under difficult conditions. Depending on the size of the wing extension, it also prevents penetration of bone residues or other undesired material from outside into the spinal canal of the vertebra. For this purpose, the wing extension is preferably provided in various sizes.

The wing extension is preferably designed such that it has a plane outer face, directed away from the pressure surface, and preferably a reinforcement rib on its inner face directed toward the pressure surface. The outer face is designed to bear in the area of the lateral resection surface of the lamina, there being no need for a force-fit bearing on the resection surface of the lamina. The smaller the gap located in between, the better the protective action against entry of material. The wing extension is expediently made in one piece with the cantilever part. For further mechanical stiffening, the reinforcement rib is provided on the inner face. In the implanted state, this reinforcement rib is located in the free space created by the resection and does not come into contact with the lamina.

The wing extension is preferably arranged in the transition area from the transverse thrust surface to the cantilever part, specifically in such a way that the wing extension extends over at most half the width of the transverse thrust surface. In this way, a maximum coverage by the wing extension is achieved without the danger of the latter penetrating too far into the resected space or into the spinal canal enclosed by the lamina, with the nerve fibers running therein. The wing extension is preferably configured such that its lower edge has a diverging orientation with respect to an axis of the anti-shear device. This means that the lower edge moves further away in the downward direction the further it is situated from the transverse thrust surface. Optimal coverage is achieved by the extension piece having a downwardly protruding configuration of this kind.

It will be noted that the wing extension, by virtue of its planar configuration on the outer face and by virtue of the reinforcement rib preferably provided on the inner face, can have an emergency bearing function. Should the fastening via the bridge part come loose, for example through failure of the anti-shear device, the lamina with its resection surface can then move only up to a point where it bears on the plane outer face of the wing extension and is supported there. This reliably avoids a collapse of the vertebral arch and the ensuing dramatic consequences for the patient.

The invention further relates to an implant set for insertion into the lamina of a vertebra, comprising a plurality of reinforcement implants of various sizes, each comprising a main body with bearing surfaces on the vertebra and a fastening device, wherein, according to the invention, a cantilever part for spanning a resected part is provided and also, at opposite ends of the cantilever part, in each case an anchoring part, wherein a first anchoring part is designed with a pressure surface for bearing on the spinous process of the vertebra, and a second anchoring part is designed with a transverse thrust surface for bearing on an outer face of the lamina, and the pressure surface and the transverse thrust surface enclose an obtuse angle, wherein an anti-shear device, in particular a facet screw, is arranged on the transverse thrust surface, and one edge of the transverse thrust surface is adjoined by a load-bearing area of the cantilever part for spanning the resected part of the lamina.

For a more detailed explanation and further optional embodiments, reference is made to the above description of the individual reinforcement implant.

BRIEF DESCRIPTION OF THE DRAWINGS

The invention is explained in more detail below on the basis of an illustrative embodiment and with reference to the attached drawing, in which:

FIG. 1 shows a bottom view of an illustrative embodiment of the reinforcement implant according to the invention;

FIGS. 2a and 2b show a plan view and a side view, respectively, of the reinforcement implant with inserted facet screws;

DETAILED DESCRIPTION OF THE INVENTION

A first illustrative embodiment of a reinforcement implant according to the invention is shown in FIG. 1. It is designated in its entirety by reference number 1. It is substantially limb-shaped, with a first limb 3 and a second limb 4, which are connected to each other by a bridge part 2.

Figure 6:
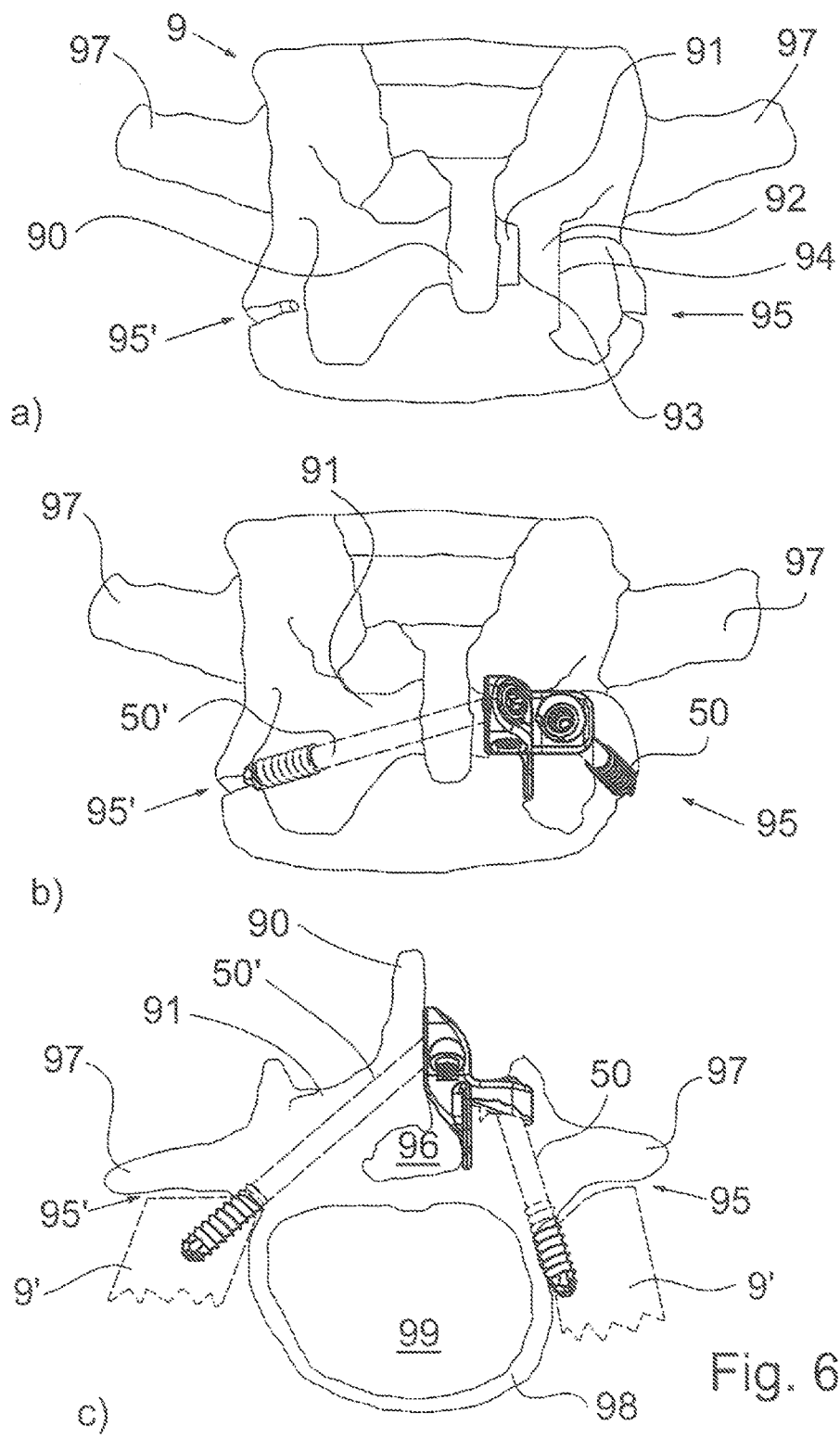
FIGS. 6a to 6c show a vertebra with a lamina resection, with and without inserted reinforcement implant according to the second embodiment in FIG. 4.

For a better understanding of the invention, there follows a detailed explanation of the structure of the vertebra and the nature of the interaction between the reinforcement implant and the vertebra. Reference is made in particular to FIGS. 6a to 6c. The vertebra 9 has a solid vertebral body 98 with two laterally protruding osseous projections 97 which, in their posterior region, are connected by an osseous arch. The osseous arch comprises a lamina 91 and, at the center thereof, a rearwardly extending projection (spinous process) 90. In the area of the transition into the lamina 91, upper and lower articular projections are arranged on each side and each form part of a facet joint 95, 95' to an adjacent lower vertebra 9'. The vertebra 9 is also connected to its adjacent lower vertebra by an intervertebral disk 99, which is arranged in a load-bearing manner between a lower cover surface of the vertebral body 98 and the corresponding upper cover surface of the lower adjacent vertebra 9'. It will be seen from the rear view in FIG. 6a that, in the area of the lamina 91, a free space 92 is present to the right of the spinous process 90. This free space was created by a resection, resulting in the formation of corresponding resection surfaces 93, 94 on the lamina 91 to the left and right of the free space 92. The opening created by this free space 92 forms an access to a spinal canal 96. It is closed and mechanically stabilized with the reinforcement implant 1 according to the invention.

As is shown in FIGS. 6a and 6b, the reinforcement implant according to the invention is mounted in place on the lamina 91 from the rear, i.e. from the posterior direction, specifically in such a way that it lies with its first limb 3 on the spinous process 90 and with its second limb 4 on the posterior face of the area of the lamina 91 directly to the right of the resection surface 94. A right-side implantation is shown in FIGS. 6a to 6c. It is equally possible to perform a left-side implantation, using a reinforcement implant with a suitable mirror-image configuration (compare FIG. 3).

To fasten the reinforcement implant 1 on the vertebra 9, a pressure surface 30 is arranged on the outer face of the first limb 3. The pressure surface 30 has a substantially plane shape. A transverse thrust surface 40 is arranged on the outer face of the second limb 4 and is designed to bear on the outer face of a lamina 91 of a vertebra 9. An anti-shear device 5 is provided for the transverse thrust surface 40. In the illustrative embodiment shown, it comprises spikes 51 (although two are shown, it is also possible to provide a smaller or a greater number) and a facet screw 50 (see FIG. 2). The facet screw 50 is oriented such that, in its normal position, its axis 55 forms an angle γ of 30° with respect to the perpendicular 67 of the transverse thrust surface 40.

The facet screw 50 is provided with a head 52, a threadless shaft 53, and a bone thread 54 at its outer end. The length of the threadless shaft 53 is such that the facet screw 50 comes to lie with the latter completely within a near-side part of the facet joint 95, while the part of the shaft with the bone thread 54 comes to lie exclusively, in a part of the facet joint on the other side, on the adjacent lower vertebra 9'. The effect of this is that, when the screw 50 is tightened, the part of the facet joint 95 on the other side is drawn toward the head 52 of the screw under the force of the bone thread 54 and is thus braced against the near-side part of the facet joint 95. This ensures reliable immobilization of the facet joint 95.

A second facet screw 50' is provided which is inserted into the first limb 3. This facet screw 50' is oriented such that it is aligned with the facet joint 95' located on the other side of the vertebra. The structure of the second facet screw 50' corresponds in principle to that of the facet screw 50. It comprises a head 52', a threadless shaft 53', and a bone thread 54'. The length of the threadless shaft 53' is significantly greater than the shaft 53, since the distance to the facet joint 95' lying on the other side is significantly greater. This second facet screw 50' is also referred to as a translaminar screw 50'.

If the intention is simply to fix the reinforcement implant 1, without immobilizing the facet joint 95, 95', the screws 50, 50' are then shorter to the extent that they are received completely within the vertebra 9, i.e. they do not protrude into the part of the facet joint on the other side on the adjacent lower vertebra 9' ("short screw"). A special screw can also be provided that has a thread along the entire length of the shaft.

The facet screws 50, 50' are not mounted rigidly in the first and second limbs 3, 4, but instead are mounted such that they are able to pivot relative to their screw axis, specifically by an angle of 15° in each direction. For this purpose, a pivot joint 6 is provided for each facet screw 50, 50' in the limb 3 and also in the limb 4. The pivot joint 6 comprises a cup-shaped seat 60, in which a ring 61 provided with a spherical jacket surface is fitted.

The two limbs 3, 4 are shaped such that they enclose an obtuse angle α with their outer faces, and with the pressure surface 30 and transverse thrust surface 40 arranged thereon. The angle α is preferably between 95° and 125°; it is 110° in the illustrative embodiment shown. By virtue of this obtuse angle, the reinforcement implant can be implanted from the dorsal direction, such that it bridges the free space 92 created by the resection on the lamina 91. For this purpose, the reinforcement implant 1 lies with its second limb 4, and with the transverse thrust surface 40 arranged thereon, on the posterior face of the lamina 91. This forms one anchoring part. The other anchoring part is formed by the first limb 3, with the pressure surface 30 which is arranged on the latter and which is pressed against a side face of the spinous process 90 of the vertebra 9. The cantilever part 2 located between the two limbs 3, 4 thus acts like a bridge spanning the free space 92 created by the resection. The force transfer lines between the two limbs 3, 4 run through a load-bearing area 20 of the cantilever part 2, specifically in such a way that the load flow takes place completely outside the free space 92. Structurally, this means that the force transfer lines in the load-bearing area 20 run in such a way that they do not intersect the plane 24 defined by the transverse thrust surface 40, but instead run exclusively outside this area (i.e. posteriorly).

In order to securely anchor the second limb 4 with its transverse thrust surface 40 to the lamina 91, and in particular to prevent an undesired shearing movement with respect to the lamina 91, an anti-shear device 5 is provided in the form both of the spikes 51 and also of the facet screw 50 as fastening pin. Each of the two devices mentioned is in itself sufficient to stop an undesired shearing movement. In order to increase the reliability of the fastening and to prevent lifting of the transverse thrust surface 40 from the outer face of the lamina 91, the facet screw 50 is provided. To prevent the undesired shearing movement, it is not strictly necessary that the screw 50 has the length shown in FIG. 2. A much shorter screw 50 is also sufficient, one which is so short that it remains completely within the vertebra 9. Only in those cases when the screw 50 is additionally intended to provide the functionality of immobilizing the facet joint 95 is the length of the screw 50 made such that it protrudes with its thread 54 from the vertebra 9 and penetrates into the lower, adjacent vertebral body 9', in order thereby to immobilize the facet joint 95.

Figure 4:
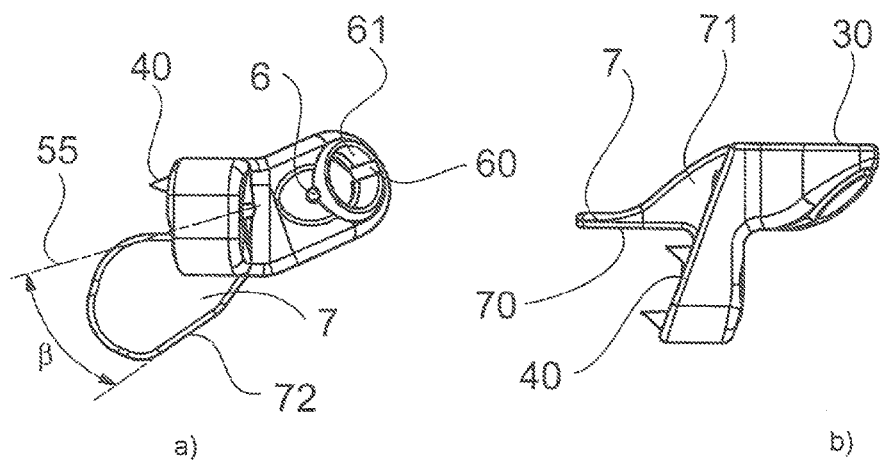
FIGS. 4a and 4b show a side view and a top view, respectively, of a second embodiment of the reinforcement implant.
Figure 5:
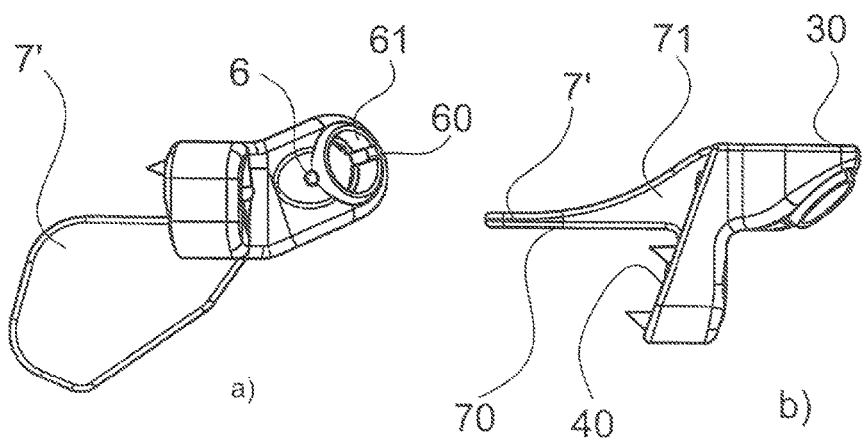
FIGS. 5a and 5b show a side view and a top view, respectively, of a third embodiment of the reinforcement implant.

In a second embodiment and third embodiment of the reinforcement implant according to the invention, as is shown in FIGS. 4 and 5, a wing extension 7 is additionally provided. Reference is made below to FIGS. 4a and 4b. The wing extension 7 protrudes from the transverse thrust surface 40. More precisely, it is arranged in the lower third of the transverse thrust surface 40 in the area of the transition between the second limb 4 and the cantilever part 2, i.e. in a transition between transverse thrust surface 40 and load-bearing 20. The wing extension 7 is oriented such that it is parallel to the pressure surface 30 on the first limb 3. The wing extension 7 has a plane surface on its outer face 70 directed toward the transverse thrust surface 40. On its opposite inner face oriented toward the pressure surface 30, it is provided with a reinforcement rib 71. The wing extension 7 comprises with its lower area the second limb 4, such that as a whole it protrudes obliquely downward (relative to the implanted state of the reinforcement implant 1'). Its lower edge 72 is oriented such that it diverges outward with respect to an axis 55 of the facet screw 50 mounted in the second limb 4. The angle of divergence β is between 15° and 20°, in the illustrative embodiment shown about 18°. Protruding obliquely downward as it does, the wing extension 7 ensures that the spinal canal 96 bounded by the lamina 91 is more effectively shielded from the penetration of bone pieces that have formed particularly during the resection of the free space 90. As far as the patient is concerned, undesired penetration of bone pieces of this kind would have the very adverse consequence of once again inducing compressive loads on the nerve fibers running in the spinal canal 96, as a result of which the desired successful outcome of the operation would no longer be achieved.

A further function of the wing extension 7 is that it additionally serves for mechanical stiffening.

On the one hand, it gives the bridge part 20 greater mechanical stability. The wing extension 7 is designed in one piece with the bridge part 20. By virtue of the plane configuration of its outer face 70, it is able to bear flush on the resection surface 94, there being no need for it to bear with a force fit. However, the smaller the gap located in between, the better the protection against penetration of material, in particular of pieces of bone as has been explained above. The smallest possible gap width also affords the advantage that the wing extension 7 can function for emergency bearing. Should the fastening of the bridge part 20 on the anchor in the second limb 4 come loose (for example if the anti-shear device 5 fails as a result of the facet screw 50 breaking), the lamina 91 with its resection surface 94 can then only move up to a point where it bears on the plane outer face 70 of the wing extension 7 and is then supported by the latter. In this way, the lamina 91 is further supported and its collapse is effectively prevented.

FIGS. 5a and 5b show a third embodiment. Compared to the second embodiment shown in FIGS. 4a and 4b, the only real difference is that a larger wing extension 7' is used. Otherwise, the explanations given above with respect to the second embodiment apply accordingly.

Figure 3:
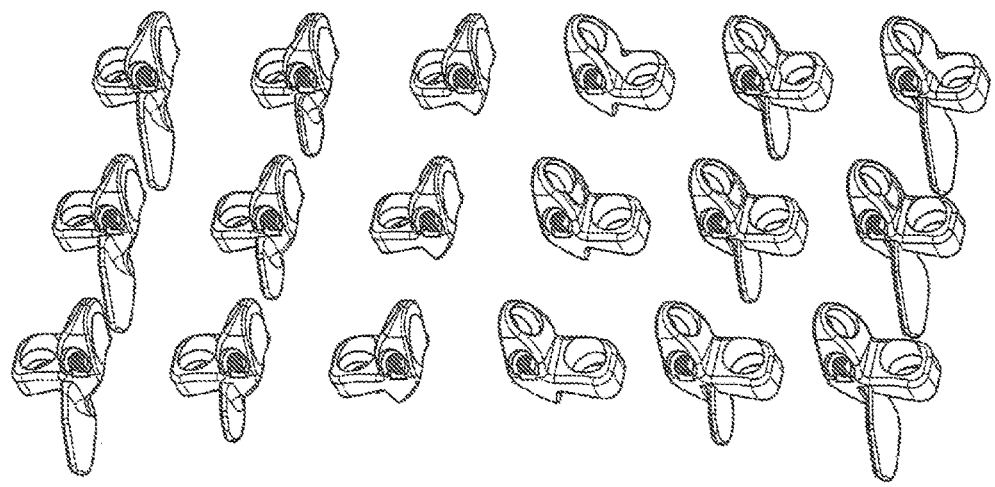
FIG. 3 shows an overview of various sizes of the reinforcement implant and of two variants.

The reinforcement implant 1 according to the invention is preferably part of an implant set, as is shown in FIG. 3. The various types, which differ in terms of their size, are shown arranged in rows. For each size, the reinforcement implant is provided both in a version for right-side implantation (right-hand half of FIG. 3) and also in a version for left-side implantation (left-hand half of FIG. 3). There is in each case a version without a wing extension, a version with a short wing extension 7, and a version with a large wing extension 7'.

The invention claimed is:

1. A reinforcement implant for insertion into a lamina of a vertebra, comprising a main body with bearing surfaces configured to bear on the vertebra and a fastening device, the main body comprising a cantilever part for spanning a resected area of the lamina and, at opposite ends of the cantilever part, a first anchoring part and a second anchoring part, the first anchoring part comprising a pressure surface for bearing on a spinous process of the vertebra, and the second anchoring part comprising a transverse thrust surface for bearing on an outer face of the lamina, the pressure surface and the transverse thrust surface enclosing an obtuse angle, and the fastening device comprising an anti-shear device arranged on the transverse thrust surface, one edge of the transverse thrust surface being adjoined by a load-bearing area of the cantilever part for transferring loading forces from the transverse thrust surface to the pressure surface, the load-bearing area being configured for spanning the resected area of the lamina, wherein the load-bearing area is configured to not intersect a plane defined by the transverse thrust surface such that the load-bearing area does not protrude into the resected area when the implant is inserted in the lamina of the vertebra, wherein the main body has a first limb on which the pressure surface is arranged and a second limb on which the transverse thrust surface is arranged, wherein at least one of the first limb and the second limb comprises a pivot joint for a fastening pin, and wherein the pivot joint is configured such that, when the pivot joint is in a center position, an axis of the fastening pin is angled relative to a perpendicular of the pressure surface for a pivot joint of the first limb or a perpendicular of the transverse thrust surface for a pivot joint of the second limb.

2. The reinforcement implant of claim 1, wherein the pivot joint has a cup-shaped receiving seat and, mounted in the cup-shaped receiving seat, a ring through which the fastening pin can be guided.

3. The reinforcement implant of claim 2, wherein the ring has a rotation barrier, which holds the ring securely against rotation with respect to the receiving seat.

4. The reinforcement implant of claim 1, wherein the pivot joint is configured such that the fastening pin is movable through 10° to 20° in each direction about a normal the center position.

5. The reinforcement implant of claim 4, wherein the first limb and the second limb each comprise a pivot joint and the pivot joints are configured such that fastening pins in the center positions of the pivot joints of the two limbs lie in one plane.

6. The reinforcement implant of claim 4, wherein, when a pivot joint of the second limb is in a center position, an axis of a fastening pin in the pivot joint is angled relative to the perpendicular of the transverse thrust surface by at most 30°.

7. The reinforcement implant of claim 4, wherein a pivot joint of the first limb is in a center position, a fastening pin in the pivot joint in an implanted state, is directed to a contralateral facet joint of the vertebra.

8. The reinforcement implant of claim 4, wherein the fastening pin is a screw that is configured to reach into an adjacent lower vertebra.

9. The reinforcement implant of claim 8, wherein the shaft of the screw has a threadless area toward a head of the screw and a thread at an end, the threadless area being dimensioned to reach as far as the adjacent lower vertebra.

10. The reinforcement implant of claim 4, wherein when the pivot joint of the second limb is in the center position, the axis of the fastening pin in the pivot joint is angled relative to the perpendicular of the transverse thrust surface by at least 10°.

11. The reinforcement implant of claim 4, wherein the fastening pin is a screw that is configured to not reach as far as into an adjacent lower vertebra and instead end within the vertebra.

12. The reinforcement implant of claim 1, wherein the anti-shear device comprises a facet screw.

13. An implant set for insertion into a lamina of a vertebra, comprising a plurality of reinforcement implants of various sizes, each comprising a main body with bearing surfaces configured to bear on the vertebra and a fastening device, the main body comprising a cantilever part for spanning a resected area of the lamina and, at opposite ends of the cantilever part, a first anchoring part and a second anchoring part, the first anchoring part comprising a pressure surface for bearing on a spinous process of the vertebra, and the second anchoring part comprising a transverse thrust surface for bearing on an outer face of the lamina, the pressure surface and the transverse thrust surface enclosing an obtuse angle, and the fastening device comprising an anti-shear device arranged on the transverse thrust surface, one edge of the transverse thrust surface being adjoined by a load-bearing area of the cantilever part for transferring loading forces from the transverse thrust surface to the pressure surface, the load-bearing area being configured for spanning the resected area of the lamina, wherein the load-bearing area is configured to not intersect a plane defined by the transverse thrust surface such that the load-bearing area does not protrude into the resected area when the implant is inserted in the lamina of the vertebra, wherein the main body has a first limb on which the pressure surface is arranged and a second limb on which the transverse thrust surface is arranged, wherein at least one of the first limb and the second limb comprises a pivot joint for a fastening pin, and wherein the pivot joint is configured such that, when the pivot joint is in a center position, an axis of the fastening pin in the pivot joint is angled relative to a perpendicular of the pressure surface for a pivot joint of the first limb or a perpendicular of the transverse thrust surface for a pivot joint of the second limb.

14. The implant set of claim 13, wherein the anti-shear device of the reinforcement implants comprises a facet screw.

15. The reinforcement implant of claim 13, wherein the fastening device comprises a facet screw.

* * * * *